US 11,480,281 B2

(12) United States Patent
Benson

(10) Patent No.: US 11,480,281 B2
(45) Date of Patent: Oct. 25, 2022

(54) SINGLE-USE DISCONNECT FLUID COUPLINGS

(71) Applicant: Colder Products Company, Roseville, MN (US)

(72) Inventor: Timothy Charles Benson, Andover, MN (US)

(73) Assignee: Colder Products Company, Roseville, MN (US)

( * ) Notice: Subject to any disclaimer, the term of this patent is extended or adjusted under 35 U.S.C. 154(b) by 0 days.

(21) Appl. No.: 17/343,248

(22) Filed: Jun. 9, 2021

(65) Prior Publication Data

US 2021/0388930 A1    Dec. 16, 2021

Related U.S. Application Data

(60) Provisional application No. 63/037,651, filed on Jun. 11, 2020.

(51) Int. Cl.
*F16L 37/30* (2006.01)
*F16L 37/34* (2006.01)

(52) U.S. Cl.
CPC .............. *F16L 37/34* (2013.01); *F16L 37/30* (2013.01); *F16L 2201/44* (2013.01)

(58) Field of Classification Search
CPC ........... F16L 29/00; F16L 29/04; F16L 37/28; F16L 37/30; F16L 37/32–36; F16L 37/38; F16L 2201/44
See application file for complete search history.

(56) References Cited

U.S. PATENT DOCUMENTS

| 4,334,551 | A  | 6/1982  | Pfister |
| 4,429,713 | A  | 2/1984  | Walter |
| 4,664,148 | A  | 5/1987  | Magnuson |
| 4,804,015 | A  | 2/1989  | Albinsson |
| 5,806,564 | A  | 9/1998  | Wilcox |
| 5,971,019 | A  | 10/1999 | Imal |
| 6,161,578 | A  | 12/2000 | Braun et al. |
| 6,237,631 | B1 | 5/2001  | Giesler et al. |
| 6,302,147 | B1 | 10/2001 | Rose et al. |
| 7,469,472 | B2 | 12/2008 | deCler et al. |
| 7,547,047 | B2 | 6/2009  | deCler et al. |
| 7,959,192 | B2 | 6/2011  | Elton et al. |
| 8,690,120 | B2 | 4/2014  | Hartnett et al. |

(Continued)

FOREIGN PATENT DOCUMENTS

| CN | 103968171 A | * | 8/2014 | .............. F16L 29/04 |
| CN | 105508775 A | * | 4/2016 | |

(Continued)

OTHER PUBLICATIONS

Machine English Translation of CN103968171 (Year: 2022).*
Machine English Translation of CN105508775 (Year: 2022).*
Machine English Translation of KR20200057325 (Year: 2022).*
Machine English Translation of FR1373480 (Year: 2022).*

(Continued)

*Primary Examiner* — Hailey K. Do
(74) *Attorney, Agent, or Firm* — Fish & Richardson P.C.

(57) ABSTRACT

Some fluid coupling devices described herein are configured for use in fluid systems for purposes of providing a single-use, disconnection functionality that can substantially limit fluid spillage when being disconnected. In some embodiments, the coupling portions cannot be functionally reconnected to each other after being disconnected from each other.

19 Claims, 6 Drawing Sheets

(56) References Cited

U.S. PATENT DOCUMENTS

| | | |
|---|---|---|
| 10,022,532 B2 | 7/2018 | Burdge |
| 2007/0073215 A1 | 3/2007 | Wieslander |
| 2008/0185056 A1 | 8/2008 | Diodati et al. |
| 2009/0051161 A1 | 2/2009 | Eskstrom |
| 2009/0076434 A1 | 3/2009 | Mischelevich |
| 2010/0183361 A1 | 7/2010 | Davis |
| 2010/0230950 A1 | 9/2010 | Scott et al. |
| 2011/0240158 A1 | 10/2011 | Py |
| 2012/0025523 A1* | 2/2012 | Zhu ............... F16L 37/0885 285/374 |
| 2012/0031515 A1 | 2/2012 | Whitaker |
| 2013/0341904 A1 | 12/2013 | Lehmann et al. |
| 2014/0345748 A1 | 11/2014 | Rogers et al. |
| 2015/0292638 A1* | 10/2015 | Pelfrey ............... F16K 17/36 251/74 |
| 2016/0158519 A1 | 6/2016 | Rhinehart |
| 2018/0296817 A1 | 10/2018 | Burdge et al. |
| 2019/0298985 A1 | 10/2019 | Truong |

FOREIGN PATENT DOCUMENTS

| | | |
|---|---|---|
| DE | 3918437 A1 * | 12/1990 |
| EP | 0028601 | 5/1981 |
| FR | 1373480 A * | 9/1964 |
| GB | 2269224 | 2/1994 |
| KR | 20200057325 A * | 5/2020 |
| WO | WO 1980/001507 | 7/1980 |
| WO | WO 2008/094707 | 8/2008 |
| WO | WO 2012/114105 | 8/2012 |
| WO | WO 2014/160756 | 10/2014 |
| WO | WO 2016/172229 | 10/2016 |
| WO | WO 2017/062859 | 4/2017 |

OTHER PUBLICATIONS

Machine English Translation of DE3918437 (Year: 2022).*
International Search Report and Written Opinion in International Appln. No. PCT/US2021/036609, dated Sep. 2, 2021, pages.

* cited by examiner

SINGLE-USE DISCONNECT FLUID COUPLINGS

CROSS-REFERENCE TO RELATED APPLICATIONS

This application claims the benefit of U.S. Provisional Application Ser. No. 63/037,651, filed Jun. 11, 2020. The disclosure of the prior application is considered part of (and is incorporated by reference in) the disclosure of this application.

BACKGROUND

1. Technical Field

This document relates to fluid coupling devices for fluid systems and methods. For example, some embodiments described in this document relate to single-use, disconnection fluid coupling devices.

2. Background Information

Fluid systems commonly include components such as tubing, pumps, reservoirs, fittings, couplings, heat exchangers, sensors, filters, valves, seals, and the like. Such components can be connected together in a network to define one or more fluid flow paths. Some fluid systems are open systems, meaning that the fluid flows through the network once and then exits the network. Other fluid systems are closed systems, meaning that the fluid recirculates within the network of components. Fluids may be moved through fluid systems using fluid pressure differentials. For example, in some cases, a pump or a vacuum source is used to create a pressure differential that causes the fluid to flow within the fluid system. In another example, gravity is used to cause the fluid to flow within the fluid system. In other examples, a combination of such techniques is used to cause the fluid to flow within the fluid system.

In the context of some fluid systems, such as some bioprocessing fluid systems, it may be desirable to have a tube coupler that can aseptically disconnect a fluid flow path. In one such example implementation, it is desirable to disconnect aseptically one or more media bags from a bioreactor system. In that scenario, an aseptic coupling can be used to disconnect the media bag(s) from the bioreactor system while substantially preventing biological contamination of the media bags and of the bioreactor via the disconnected ends of the coupling during and after the disconnection process. Such an aseptic coupling will also serve to limit the exposure of the fluid to the surrounding environment.

SUMMARY

This document describes fluid coupling devices for fluid systems and methods. In some embodiments, the fluid coupling devices can be implemented as single-use, disconnection fluid coupling devices that are configured to reduce the likelihood of fluid spillage when being disconnected. In some embodiments, the coupling portions cannot be reconnected to each other after being disconnected from each other. Accordingly, the fluid coupling devices are called "single-use" disconnect couplings. In the context of this disclosure, the term "fluid" includes anything that flows, e.g., gases, liquids, steam, vapors, gels, mists, and powders.

In particular embodiments, the fluid coupling devices described herein are single-use devices because, after the two portions of the coupling (also referred to herein as "coupling halves" and/or "connectors") are disconnected from each other, the fluid paths of one or both portions are irreversibly blocked. Hence, in these particular embodiments, the fluid coupling devices provided herein are structurally configured to be single-use disconnection devices so that, after the single-use coupling halves have been disconnected from each other, they cannot be operably reconnected to each other (or to any other coupling halves) so as to reestablish an open fluid flow path therethrough.

Additionally, in such single-use embodiments or in other embodiments, the fluid coupling devices can be configured as "aseptic" coupling devices in that, during disconnection and after the two portions of the coupling device are disconnected from each other, the fluid paths of both portions are mechanically blocked, e.g., by a valve, so as to inhibit biological contamination migrating into the flow paths. Such an "aseptic" coupling will also serve to limit the exposure of the fluid to the surrounding environment.

In one aspect, this disclosure is directed to a fluid coupling device. For example, this disclosure is directed to a single-use fluid coupling device that includes: (i) a first coupling comprising a valve; (ii) a second coupling comprising a valve, the second coupling configured to be releasably coupled together with the first coupling; and (iii) a removable sleeve configured to be releasably engaged with the first and second couplings while the first and second couplings are coupled together. While the removable sleeve is engaged with the first and second couplings, the removable sleeve holds open each of the valves of the first and second couplings. The first and second couplings are configured such that, when the removable sleeve is separated from the first and second couplings, the valves of the first and second couplings close.

Such a single-use fluid coupling device may optionally include one or more of the following features. In some embodiments, the single-use fluid coupling device is a single-use aseptic fluid coupling device. While the removable sleeve is engaged with the first and second couplings, the removable sleeve can be engaged with respective valves within the first and second couplings. Any type of valves can be included within the first and second couplings. In some embodiments, while the removable sleeve is engaged with the first and second couplings, the removable sleeve can be engaged with respective poppets of the valves of the first and second couplings. In some embodiments, the valves of the first and second couplings are spring-biased to close. While the removable sleeve is engaged with the first and second couplings, the removable sleeve directly may contact movable poppets of each of the valves of the first and second couplings. In some embodiments, the first and second couplings are identical. In some embodiments, the removable sleeve retains the first coupling releasably coupled with the second coupling while the removable sleeve is releasably engaged with the first and second couplings. The first coupling may include a first main body and the second coupling may include a second main body. The first and second main bodies may each define one or more openings through an outer wall of the main bodies. The removable sleeve may include radially extending projections that extend through the one or more openings through the outer wall of the main bodies. The radially extending projections may engage in annular grooves defined by the valves of the first and second couplings. The first coupling may include a projection that is releasably engaged with a receptacle of the second coupling. The removable sleeve may define a relief area that receives the projection that is releasably engaged with the receptacle. The removable sleeve may extend more than 180 degrees around an outer circumference of the first and second couplings. The removable sleeve may be manually deflectable to allow disengagement of the removable sleeve from the first and second couplings. The first coupling may include a first main body and the second coupling may include a second main body. The first main body may define two openings through the first main body, and the second main body may define two openings through the second main body. The removable sleeve may include four radially extending projections that extend through the two openings through the first main body and the two openings through the second main body. In some embodiments, two of the four radially extending projections are engaged in an annular groove defined by the valve of the first coupling, and two of the four radially extending projections are engaged in an annular groove defined by the valve of the second coupling. After removal of the removable sleeve from engagement with the first and second couplings, the removable sleeve may not be engageable with the first and second couplings so as to hold open each of the valves of the first and second couplings.

Particular embodiments of the subject matter described in this document can be implemented to realize one or more of the following advantages. First, the coupling halves of the fluid coupling devices provided herein are designed so that the uncoupling process involves closing valves in a particular sequence so that spillage related to fluid inclusion is eliminated or minimized.

Second, in some embodiments, the fluid coupling devices are designed to have a minimal number of components so that the fluid coupling devices are economical.

Third, some embodiments of the fluid coupling devices provide an improved non-spill aseptic disconnection capability that may optionally reduce or eliminate the need for sterile rooms or sterile benchtop environments in some cases. As such, these embodiments of the aseptic fluid coupling devices described herein may facilitate efficient and cost-effective operations or uses that would otherwise be high-cost or even cost prohibitive in some traditional settings that required the disconnection of particular fluid couplings in a sterile room or within a sterile flow-hood to prevent biological contamination.

Fourth, some embodiments of the fluid coupling devices provided herein are advantageously designed to be single use couplings that cannot be operatively reconnected to reestablish an open flow path therethrough. Accordingly, the potential for contamination from reuse is prevented.

Unless otherwise defined, all technical and scientific terms used herein have the same meaning as commonly understood by one of ordinary skill in the art to which this disclosure pertains. In addition, the materials, methods, and examples of the embodiments described herein are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION OF ILLUSTRATIVE EMBODIMENTS

Figure 1:
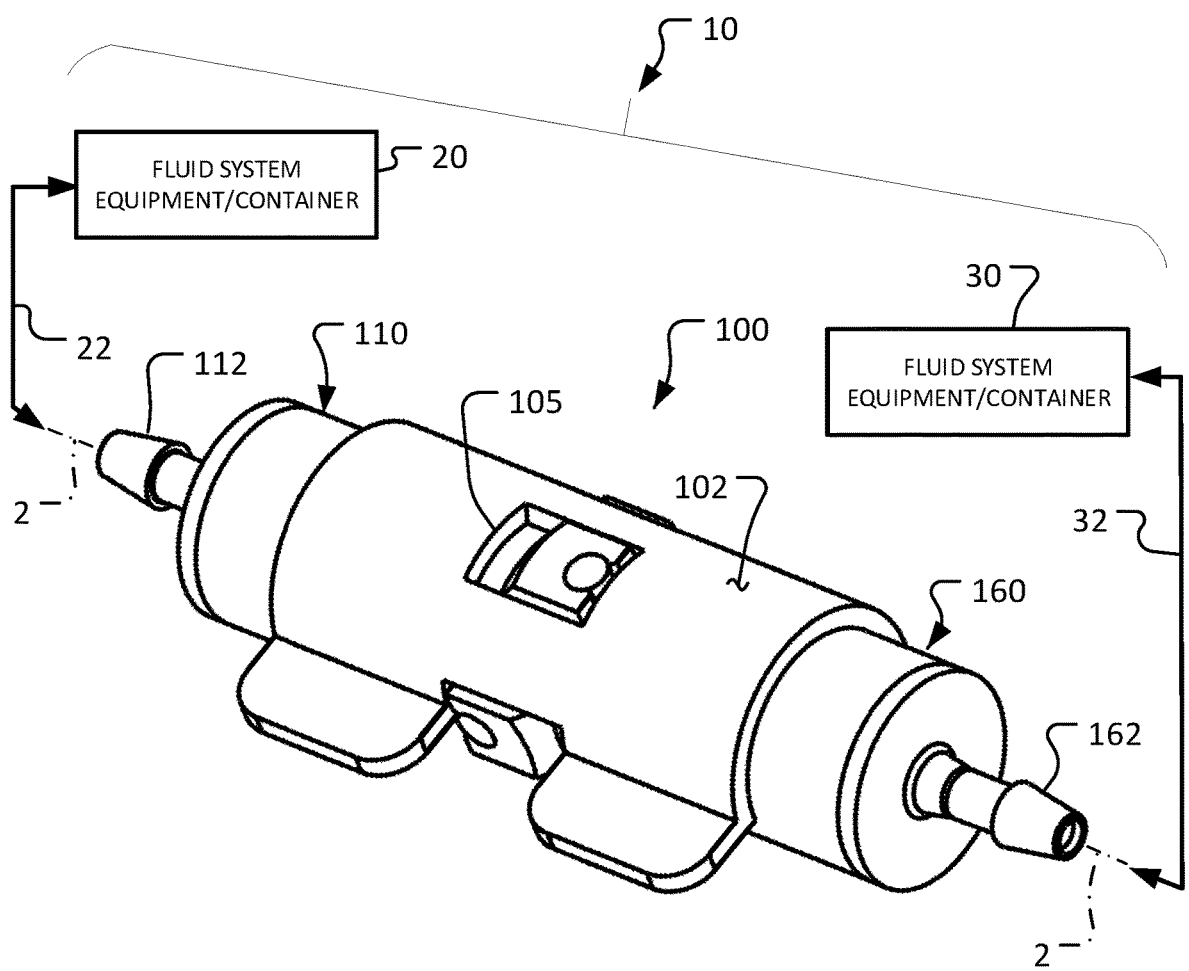
FIG. 1 is a perspective view of an example fluid system including an example fluid coupling device arranged in an operative connected configuration, in accordance with some embodiments provided herein.

Referring to FIG. 1, some example embodiments of a fluid system 10 include one or more example fluid coupling devices 100 configured to, for example, releasably connect a first fluid system equipment or container 20 to a second fluid system equipment or container 30. In some implementations, the fluid system 10 may include at least one fluid coupling device 100 that is a single-use, aseptic disconnection fluid coupling device, in which first and second mating components 110 and 160 are configured to disconnect from one another in a manner that provides an aseptic disconnection and that mechanically prevents reconnection and reuse of the fluid path through the mating components 110 and 160. (The first and second mating portions 110 and 160 are sometimes referred to herein as "couplings," "coupling devices," "coupling halves," or a "coupling-half.")

In one non-limiting example, the fluid coupling 100 can provide a single-use, aseptic disconnection capability for a fluid path between the fluid system equipment 20 in the form of a bioreactor system (connected directly to the coupling device 100 or connected via a fluid tube 22) and the fluid system container 30 in the form of a media bag (connected directly to the coupling device 100 or connected via a fluid tube 32). It should be understood that the fluid coupling 100 does not specifically need to be an "aseptic" fluid coupling in all embodiments.

Figure 2:
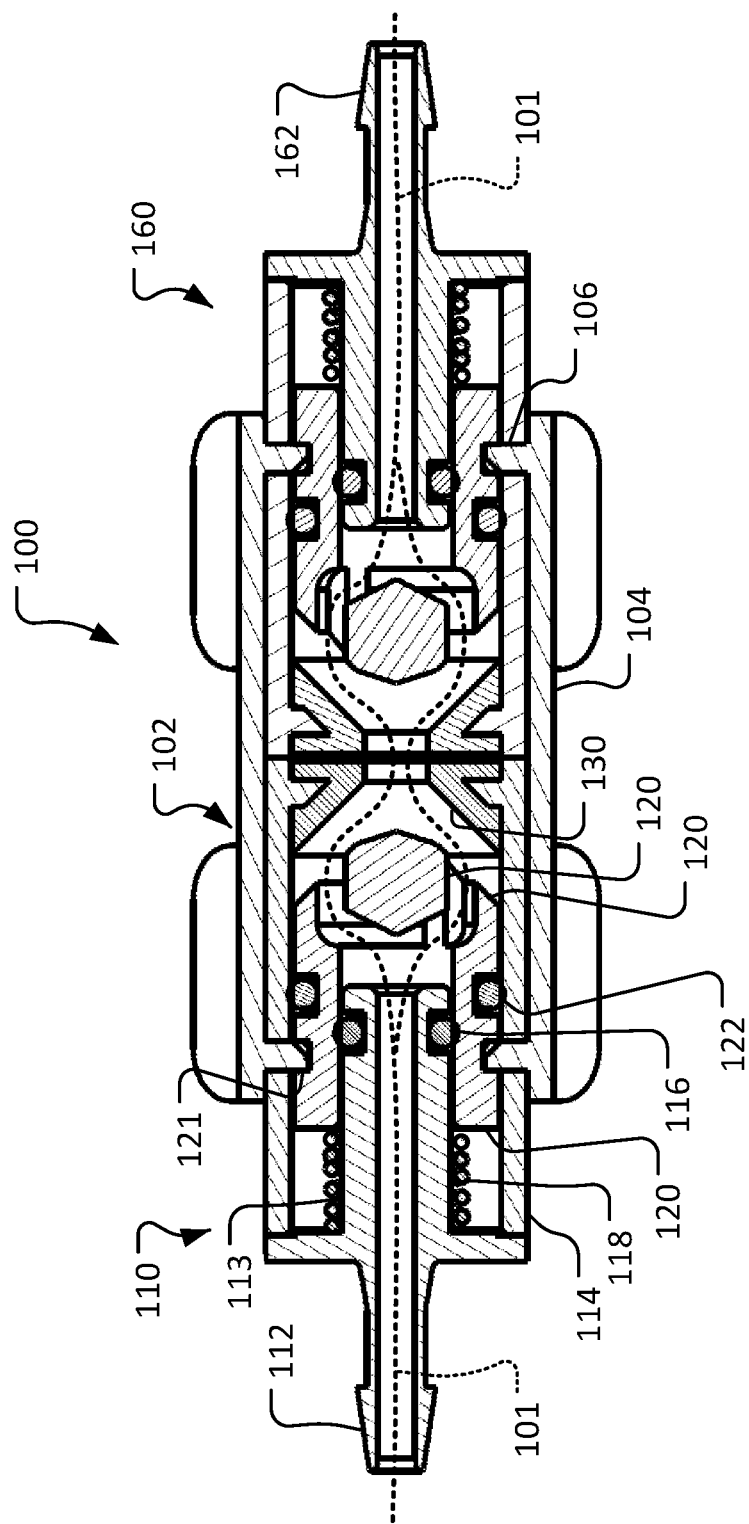
FIG. 2 is a longitudinal cross-section view of the fluid coupling device of FIG. 1 arranged in the operative connected configuration.

Generally, the coupling 100 is provided to an end user in the coupled arrangement (as depicted), and with a removable sleeve 102 surrounding the coupled mating components 110 and 160, as depicted in FIGS. 1 and 2. In some cases, the coupling 100 is sterile or made to be sterilized. Each coupling-half 110 and 160, as well as the assembled coupling 100 overall, defines a longitudinal axis 2.

Still referring to FIGS. 1 and 2, the fluid coupling 100 in the depicted embodiment includes the removable sleeve 102 and the mating components 110 and 160 in the form of a first coupling 110 and a second coupling 160. The first coupling 110 and the second coupling 160 are releasably coupled to each other. The first and second couplings 110 and 160 are shown fully coupled (connected) in FIGS. 1 and 2, such that an open flow path 101 is provided through the fluid coupling 100. That is, in the fully coupled, operable configuration as shown, fluid can flow through the coupling 100 between a first connection 112 and a second connection 162.

While the first and second connections 112 and 162 are depicted as barbed connections, it should be understood that the coupling halves 110 and 160 can have any type of connections such as, but not limited to, threaded connections, elbows, tees, sanitary fittings, compression fittings, and the like, and combinations thereof.

The materials from which one or more of the components of the fluid coupling 100 are made of include thermoplastics or thermosets. In particular embodiments, the materials from which the components of the fluid coupling 100 are made of are thermoplastics, such as, but not limited to, ABS, acetal, polycarbonate, polysulfone, polyether ether ketone, polysulphide, polyester, polyvinylidene fluoride (PVDF), polyethylene, polyphenylsulfone (PPSU; e.g., Radel®), polyetherimide (PEI; e.g., Ultem®), polypropylene, polyphenylene, polyaryletherketone, and the like, and combinations thereof. In some embodiments, the materials from which one or more of the components of the fluid coupling 100 are made of include metals such as, but not limited to stainless steel, brass, aluminum, plated steel, and the like. In particular embodiments, one or both of the coupling halves 110 and 160 is/are metallic-free. In some embodiments, one or both of the coupling halves 110 and/or 160 includes one or more plastic or metallic spring members (e.g., spring steel, stainless steel, piano wire, and the like). In certain embodiments, fluid coupling 100 includes one or more gaskets, seals, and/or valve seats that are made of materials such as, but not limited to, silicone, fluoroelastomers (FKM), ethylene propylene diene monomer (EPDM), thermoplastic elastomers (TPE), buna, buna-N, thermoplastic vulcanizates (TPV), and the like.

In the depicted embodiment, the first coupling 110 and the second coupling 160 are constructed exactly that same as each other. Accordingly, the following description will focus on the first coupling 110, but it should be understood that the same description applies to the second coupling 160 as well. In some embodiments, the first coupling 110 and the second coupling 160 can be constructed different from each other.

Referring to FIG. 2, the components of the first coupling 110 will now be described. The first coupling 110 includes a main body 114, a poppet 120, a spring 118, an inner sleeve 113, a valve seat 130, and the first connection 112.

The poppet 120 (also shown in FIGS. 7 and 8) is slidably disposed between the outer diameter of the sleeve 113 and the inner diameter of the main body 114. A seal member 116 resides between the sleeve 113 and the poppet 120. Another seal member 122 resides between the poppet 120 and the main body 114.

Figure 4:
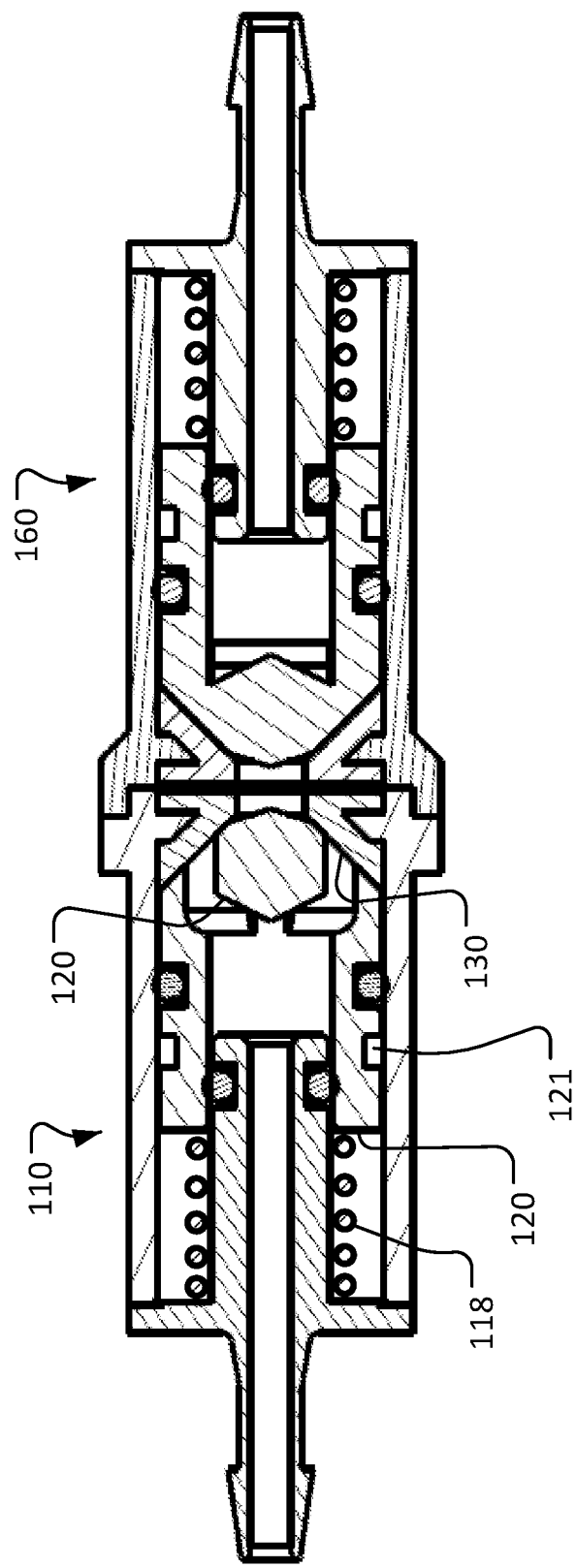
FIG. 4 is a longitudinal cross-sectional view of the fluid coupling device of FIG. 1 in the first state during disconnection of the fluid coupling device.

The spring 118 biases the poppet 120 toward the valve seat 130. When the poppet 120 is in contact with the valve seat 130, no open flow path through the first coupling 110 exists. This is shown in FIG. 4, for example. The valve seat 130 can be made of materials such as, but not limited to, silicone, fluoroelastomers (FKM), ethylene propylene diene monomer (EPDM), thermoplastic elastomers (TPE), buna, buna-N, thermoplastic vulcanizates (TPV), and the like.

In the operative connected configuration of the fluid coupling 100 (as depicted in FIGS. 1 and 2), the poppet 120 is in its open configuration in which the poppet 120 is spaced apart from the valve seat 130. Accordingly, the open flow path 101 extends through each of the first coupling 110 and the second coupling 160.

Even though the spring 118 is trying to push the poppet 120 into contact with the valve seat 130, the poppet 120 is retained from moving by the removable sleeve 102. In particular, the removable sleeve 102 includes one or more radially extending projections 106 that engage in a groove defined by the poppet 120 (transverse to the longitudinal axis 2) to thereby retain the poppet 120 in its open configuration as shown. The projections 106 are also visible in FIG. 3.

While in the depicted embodiment, the valves are depicted as poppet valves, it should be understood that any type and design of valve can be used for the fluid coupling 100. The same basic concepts apply. That is, the removable sleeve 102 can engage a member of the valves to hold the valves in the open position.

Figure 3:
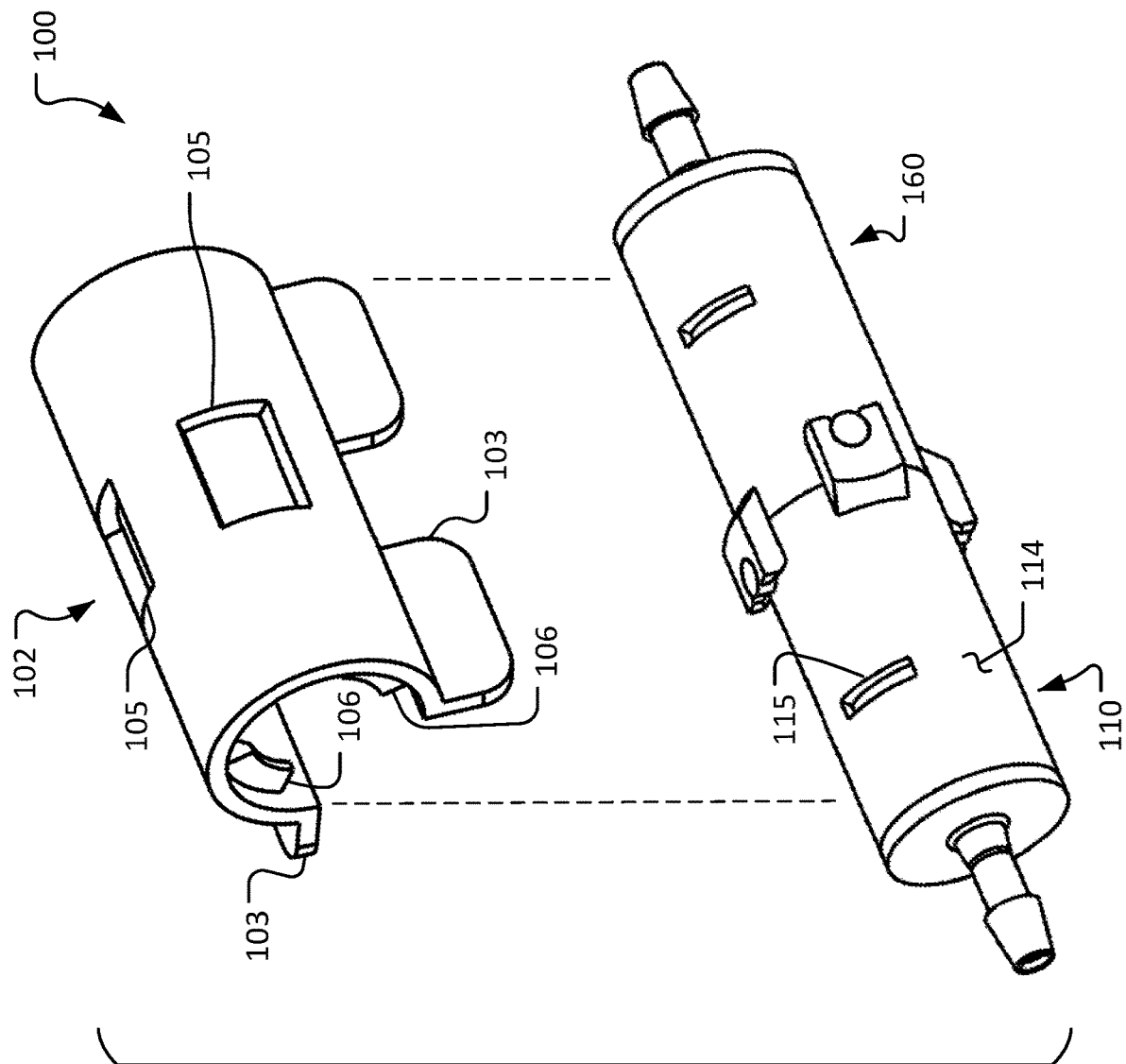
FIG. 3 is a perspective view of the fluid coupling device of FIG. 1 in a first state during disconnection of the fluid coupling device.

FIG. 3 depicts a first stage of decoupling the fluid coupling 100. That is, the removable sleeve 102 has been detached from its engagement with the first and second couplings 110/160. As described further below, the disengagement of the removable sleeve 102 from the first and second couplings 110/160 releases the poppets of the first and second couplings 110/160 so that the springs push the poppets into contact with the valve seats to eliminate the open flow path 101.

The removable sleeve 102 is a flexible member such that, while extending more than 180 degrees around the circumference of the first and second couplings 110/160, the removable sleeve 102 can be manually deflected, removed/detached, and separated from the first and second couplings 110/160. One or more convenient thumb tabs 103 can be included to help facilitate the manual deflection and subsequent removal of the removable sleeve 102 from the first and second couplings 110/160. In some embodiments, the removable sleeve 102 is or includes a tear-away member.

In FIG. 3, it can be seen that the radially extending projections 106 of the removable sleeve 102 extend through openings 115 defined by the outer wall of the main body 114. In the depicted embodiment, each of the first and second couplings 110/160 includes two openings 115 (180 degrees opposed to each other), and the removable sleeve 102 corresponding includes four radially extending projections 106. However, in some embodiments each of the first and second couplings 110/160 includes a single opening 115, and the removable sleeve 102 corresponding includes two radially extending projections 106 (one for each of the first and second couplings 110/160). Other configurations are also possible.

Figure 8:
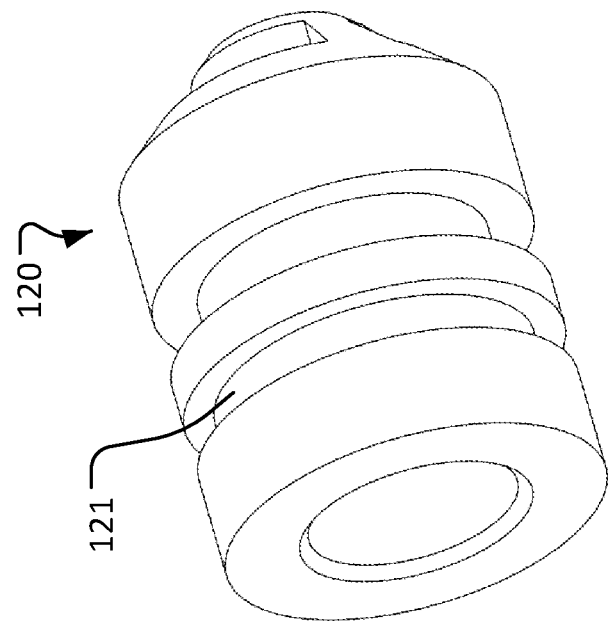
FIG. 8 is a second perspective view of the poppet component of FIG. 7.
Figure 7:
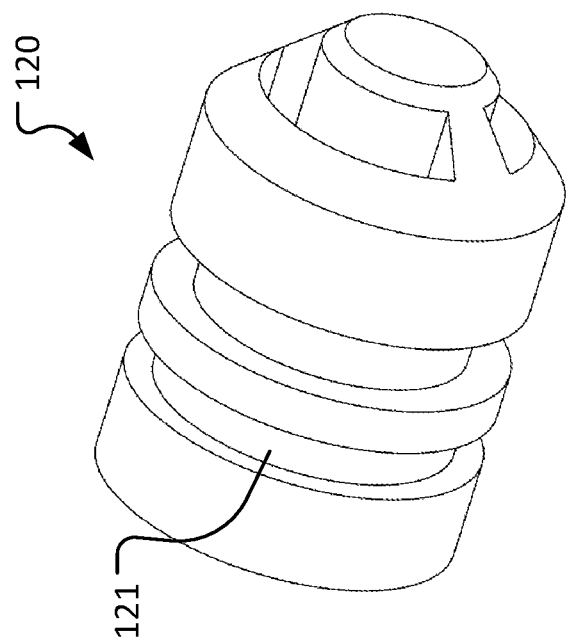
FIG. 7 is a first perspective view of an example poppet component of the fluid coupling device of FIG. 1.

Now again with respect to the first coupling 110 in particular (as an example for both couplings 110/160), while the removable sleeve 102 is engaged on the first and second couplings 110/160, the radially extending projections 106 extend through the openings 115 and then into an annular groove 121 defined by the poppet 120 (see FIGS. 2, 7, and 8). That engagement between the radially extending projections 106 and the annular groove 121 defined by the poppet 120 holds the poppet 120 in its open position (see FIG. 2). However, when the removable sleeve 102 is uncoupled from the first and second couplings 110/160 (as depicted in FIG. 3), then the radially extending projections 106 are no longer engaged in the annular groove 121 defined by the poppet 120.

Accordingly, the poppet 120 is then free to be pushed by the spring 118 against the valve seat 130. The poppet 120 seals against the valve seat 130 to block fluid flow through the first coupling 110. For that reason, when the removable sleeve 102 is separated from first and second couplings 110/160 the previously open fluid flow path 101 (FIG. 2) is no longer open. That is, the act of manually removing the removable sleeve 102 from the first and second couplings 110/160 results in closing/blocking the fluid flow path therethrough.

FIG. 4 depicts the first and second couplings 110/160 without the removable sleeve 102. Accordingly, the poppet 120 is seated against the valve seat 130 so as to close the fluid flow through the first coupling 110. The second coupling 160 (being the same as the first coupling 110) also has no open fluid flow path therethrough. With the fluid flow paths of both the first and second couplings 110/160 closed, then the first and second couplings 110/160 can be separated from each other.

Figure 5:
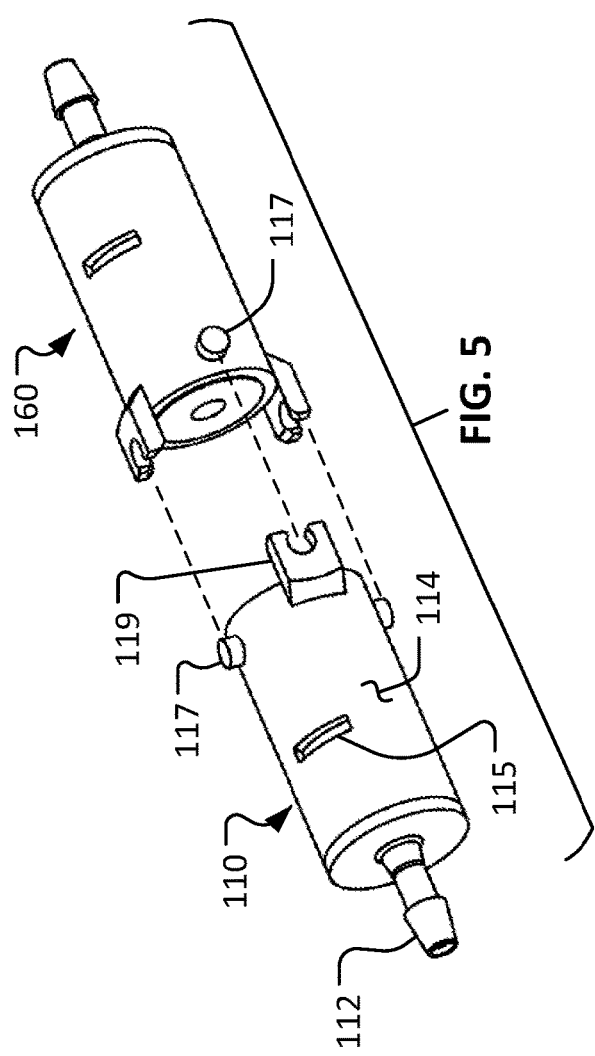
FIG. 5 is a perspective view of the fluid coupling device of FIG. 1 in a second state during disconnection of the fluid coupling device.
Figure 6:
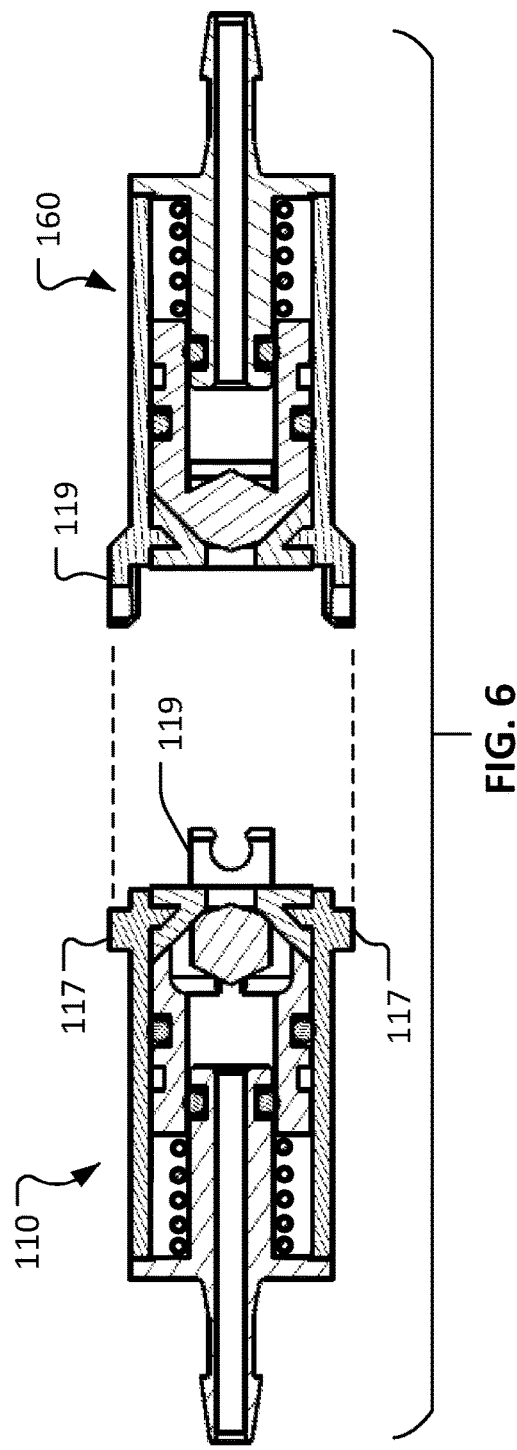
FIG. 6 is a longitudinal cross-sectional view of the fluid coupling device of FIG. 1 in the second state during disconnection of the fluid coupling device.

FIGS. 5 and 6 depict the first and second couplings 110/160 separated from each other, in a final state of disconnection. Here we can see that the first and second couplings 110/160 include mechanical engagement features by which the first and second couplings 110/160 can be properly aligned and releasably coupled to each other. That is, the first coupling 110 (again as an example also for the second coupling 160) includes a pair of projections 117 (arranged 180 degrees opposite from each other) and a pair of receptacles 119 (arranged 180 degrees opposite from each other and 90 degrees offset from the projections 117). The receptacles 119 are configured to releasably receive the projections 117. In some embodiments, the projections 117 can be manually snapped into and out of the receptacles 119. Accordingly, the engagement by the projections 117 and receptacles 119 can be used to maintain the first and second couplings 110/160 releasably engaged together. Such an arrangement of the pair of projections 117 and the pair of receptacles 119 facilitates the releasable coupling of first and second couplings 110/160 together.

In the depicted embodiment, the pair of projections 117 and the pair of receptacles 119 extend radially outward from the outer diameter of the main body 114. Accordingly, the removable sleeve 102 defines one or more openings 105 (relief areas) to receive the projections 117 and receptacles 119 (see FIGS. 1 and 3).

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A single-use fluid coupling device, comprising:
   a first coupling comprising a valve;
   a second coupling releasably coupled to the first coupling and comprising a valve; and
   a removable sleeve releasably engaged with the first and second couplings, wherein the removable sleeve holds open each of the valves of the first and second couplings,
   wherein the first and second couplings are configured such that, when the removable sleeve is separated from the first and second couplings, the valves of the first and second couplings close, and
   wherein while the removable sleeve is engaged with the first and second couplings, the removable sleeve directly contacts movable poppets of each of the valves of the first and second couplings.

2. The single-use fluid coupling device of claim 1, wherein, while the removable sleeve is engaged with the first and second couplings, the removable sleeve is engaged with respective poppets of the valves of the first and second couplings.

3. The single-use fluid coupling device of claim 1, wherein the valves of the first and second couplings are spring-biased to close.

4. The single-use fluid coupling device of claim 1, wherein the first and second couplings are identical.

5. The single-use fluid coupling device of claim 1, wherein the single-use fluid coupling device is a single-use aseptic fluid coupling device.

6. The single-use fluid coupling device of claim 1, wherein, after removal of the removable sleeve from engagement with the first and second couplings, the removable sleeve is not engageable with the first and second couplings so as to hold open each of the valves of the first and second couplings.

7. The single-use fluid coupling device of claim 1, wherein the removable sleeve retains the first coupling releasably coupled with the second coupling while the removable sleeve is releasably engaged with the first and second couplings.

8. The single-use fluid coupling device of claim 1, wherein the first coupling includes a projection that is releasably engaged with a receptacle of the second coupling.

9. The single-use fluid coupling device of claim 8, wherein the removable sleeve defines a relief area that receives the projection that is releasably engaged with the receptacle.

10. The single-use fluid coupling device of claim 1, wherein the removable sleeve extends more than 180 degrees around an outer circumference of the first and second couplings.

11. The single-use fluid coupling device of claim 10, wherein the removable sleeve is manually deflectable to allow disengagement of the removable sleeve from the first and second couplings.

12. The single-use fluid coupling device of claim 1, wherein the first coupling includes a first main body and the second coupling includes a second main body, wherein the first and second main bodies each define one or more openings through a respective outer wall of the first and second main bodies.

13. The single-use fluid coupling device of claim 12, wherein the removable sleeve includes radially extending projections that extend through the one or more openings through the respective outer walls of the first and second main bodies.

14. The single-use fluid coupling device of claim 13, wherein the radially extending projections engage in annular grooves defined by the valves of the first and second couplings.

15. The single-use fluid coupling device of claim 1, wherein the first coupling includes a first main body and the second coupling includes a second main body, wherein the first main body defines two openings through the first main body, and wherein the second main body defines two openings through the second main body.

16. The single-use fluid coupling device of claim 15, wherein the removable sleeve includes four radially extending projections that extend through the two openings through the first main body and the two openings through the second main body.

17. The single-use fluid coupling device of claim 16, wherein two of the four radially extending projections are engaged in an annular groove defined by the valve of the first coupling, and wherein two of the four radially extending projections are engaged in an annular groove defined by the valve of the second coupling.

18. A single-use fluid coupling device, comprising:
a first coupling comprising a valve;
a second coupling comprising a valve, the second coupling configured to be releasably coupled together with the first coupling; and
a removable sleeve configured to be releasably engaged with the first and second couplings while the first and second couplings are coupled together,
wherein, while the removable sleeve is engaged with the first and second couplings, the valves of the first and second couplings are each open,
wherein, when the removable sleeve is separated from the first and second couplings, the valves of the first and second couplings close,
wherein the first coupling includes a first main body and the second coupling includes a second main body,
wherein the first main body defines one or more openings through the first main body, wherein the second main body defines one or more openings through the second main body,
wherein the removable sleeve includes radially extending projections that extend through the one or more openings through the first main body and the one or more openings through the second main body, and
wherein the radially extending projections engage in annular grooves defined by the valves of the first and second couplings.

19. The single-use fluid coupling device of claim 18, wherein the valves of the first and second couplings are spring-biased to close.

* * * * *